(12) United States Patent
Ma et al.

(10) Patent No.: US 11,084,035 B2
(45) Date of Patent: Aug. 10, 2021

(54) APPARATUS FOR CELL PREPARATION

(71) Applicant: Shenzhen Eureka biotechnology Co. Ltd, Guangdong (CN)

(72) Inventors: Mo Ma, Shenzhen (CN); Bofu Xue, Shenzhen (CN)

(*) Notice: Subject to any disclaimer, the term of this patent is extended or adjusted under 35 U.S.C. 154(b) by 223 days.

(21) Appl. No.: 16/256,802

(22) Filed: Jan. 24, 2019

(65) Prior Publication Data

US 2020/0122145 A1    Apr. 23, 2020

(30) Foreign Application Priority Data

Oct. 17, 2018 (CN) .......................... 201811207844.8
Oct. 17, 2018 (CN) .......................... 201811207845.2
Oct. 17, 2018 (CN) .......................... 201811207847.1

(51) Int. Cl.
*B01L 3/00*    (2006.01)

(52) U.S. Cl.
CPC ... *B01L 3/502761* (2013.01); *B01L 3/502715* (2013.01); *B01L 2300/048* (2013.01); *B01L 2300/0627* (2013.01); *B01L 2300/087* (2013.01)

(58) Field of Classification Search
CPC ......... B01L 3/502761; B01L 3/502715; B01L 2300/087; B01L 2300/0627; B01L 2300/048; A61M 1/0218; A61M 1/3618; A61M 1/3693; A61M 1/0209; A61M 2205/3393; A61M 2205/7545; A61M 2205/3368

See application file for complete search history.

(56) References Cited

U.S. PATENT DOCUMENTS

| | | | | |
|---|---|---|---|---|
| 4,416,654 A | * | 11/1983 | Schoendorfer | A61M 1/3693 494/10 |
| 5,643,193 A | * | 7/1997 | Papillon | A61M 1/3621 604/6.07 |
| 2008/0311651 A1 | * | 12/2008 | Coelho | A61M 1/0281 435/307.1 |
| 2009/0211989 A1 | * | 8/2009 | Nguyen | B01D 21/302 210/767 |

* cited by examiner

*Primary Examiner* — Michael L Hobbs
(74) *Attorney, Agent, or Firm* — Feng Qian

(57) ABSTRACT

The disclosure provides an apparatus for processing a blood sample, a device for cells preparation and a method thereof. The disclosure can be used for blood separation, cell culture and preparation of cells. The apparatus mainly uses a weight sensor to have the weight and some liquid sensors. By optimizing the connection relationship of each device in the whole equipment, simplifying the operation process of the equipment, coordinating each step of the device, reducing the production cost, integrating the steps of PBMC cell separation and magnetic bead separation, the method makes the cell preparation process more intelligently automated, the operation simpler, the cell pollution reduced and the success rate of cell preparation improved. It has broad application prospects and huge market value.

28 Claims, 8 Drawing Sheets

APPARATUS FOR CELL PREPARATION

CROSS-REFERENCE TO RELATED PATENT APPLICATION

This application claims priority to and the benefit of, Chinese Patent Application Serial No. 201811207847.1, filed on Oct. 17, 2018, entitled "Method for Cell Preparation" by Ma et al. The entire disclosure of the above-identified application is incorporated herein by reference. This application claims priority to and the benefit of, Chinese Patent Application Serial No. 201811207845.2, filed on Oct. 17, 2018, entitled "Method for Cell Preparation" by Ma et al. The entire disclosure of the above-identified application is incorporated herein by reference. This application claims priority to and the benefit of, Chinese Patent Application Serial No. 201811207844.8, filed on Oct. 17, 2018, entitled "Method for Cell Preparation" by Ma et al. The entire disclosure of the above-identified application is incorporated herein by reference.

Some references, which may include patents, patent applications, and various publications, are cited and discussed in the description of the present disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference is individually incorporated by reference.

TECHNICAL FIELD

The disclosure relates to the field of biomedical technology, and more particularly relates to an apparatus for preparing cells.

BACKGROUND

Cell therapy is a treatment method which separates and extracts some cells from human or animal tissues, blood, etc. and transfuses them directly to human or animal, or transfuses the extracted cells back to human or animal by means of screening, gene modification, induced differentiation, cultivation and amplification, etc. Cellular immunotherapy (CIT) is a rapid development cell therapy for many diseases in recent years. It can cure diseases by reinfusion of lymphocytes from tissues or blood which are screened, modified, induced and amplified in vitro. Common applications include preparation of dendritic cells (DC), T cells and NK cells for cancer treatment, and preparation of Treg cell for treatment of autoimmune diseases and infertility, allergies, viral infections and many other diseases.

Cell preparation refers to the preparation of cells used in cell therapy. For example, killer T cells used in cancer therapy can generally be divided into many steps: peripheral blood collection→peripheral blood mononuclear cells (PBMC) separation→specific lymphocyte populations separation→cells activation→cells incubation→virus transfection→cells amplification→cell concentration and washing→preparations after cells washing→cells reinfusion. According to different technical principles and clinical application requirements, the above process steps can be properly combined and adjusted. For example, the process of cytokine-induced killer cell (CIK) therapy can be summarized as follows: peripheral blood collection→peripheral blood mononuclear cells (PBMC) separation→cells activation→cells incubation→cells amplification→cells preparations after cells washing→cells reinfusion. Chimeric antigen receptor T cell (CAR-T) immunotherapy is an advanced and complex representative of cell therapy technology at present. The preparation of CAR-T cells needs to complete most or all of the above-mentioned cell preparation processes. Chimeric antigen receptor T cell (CAR-T) immunotherapy is an advanced and complex representative of cell therapy technology at present. The preparation of CAR-T cells needs to complete most or all of the above-mentioned cell preparation processes. Because CAR-T technology is not long before it comes into being and its technology is complex, and there is no automation equipment specially developed and optimized for it on the market. Most of the cell preparation processes in clinical research of CAR-T therapy are still based on the manual preparation methods in similar laboratories. With the development of cell therapy industry, more and more attention has been paid to the consistency of cell preparation. How to overcome the problems of microbial contamination and cross-contamination between samples caused by open manual preparation and batch difference caused by the proficiency of different operators is an important basis for promoting cell therapy technology to achieve the final standard of cell drug preparation. Therefore, it is very important to use automated equipment to complete a single step in the cell preparation process and to achieve the minimum and stable batch gap. Even on the premise of the stable realization of each step, using automated equipment to complete multiple steps of cell preparation will be an important means to complete the cell therapy technology towards the standard of cell drug preparation.

In one example, Chinese Patent Publication CN1331610A presents a system for separating biological liquids as components, including a set of containers for receiving biological liquids that will be separated and already separated components, an alternative container for accepting additive solutions, and a hollow centrifugal processing chamber with an axial inlet/outlet of biological liquids. The processing chamber has a movable piston for introducing quantitative biological liquids and extruding the processed biological liquids through the outlet. Optical devices monitor piston positions to control the extrusion of intake fluids and components; a pressure regulating valve device selectively connects processing chambers and containers, or disconnects their connections; and the system displayed is operated in independent and non-independent transfer modes, especially for adding antiseptic solutions to separated hematopoietic stem cells. In the independent mode, the liquid is sucked into the processing chamber, centrifuged and separated into components, which are extruded as far as possible by density gradient products; in the transfer mode, the processing chamber sucks and extrudes the liquid in a stationary condition, and valve actuators use piston motion to transfer liquid from one container to another through the treatment chamber without centrifugation or separation, while devices used to monitor piston position control the amount of unseparated liquid transferred.

In one example, Chinese Patent Publication CN105263611A presents a mixing device for mixing biological specimens contained in flexible storage bags at controlled temperatures. The mixing device includes a bracket for supporting a storage bag containing biological specimens to be mixed and for shifting specimens in the storage bag on the bracket to mix specimens. A temperature control device holds the specimen at a controlled temperature during mixing, and a component for shifting the specimen includes at least one expandable/contractible bag, i.e., a gas bag, and when expanding, at least one expandable/contractible bag contacts directly the surface of a portion of the storage bag to gradually squeeze the storage bag, and make the specimen contained move to the part of the storage bag.

In one example, Chinese Patent Publication CN101146559A presents a system for the extraction, collection, processing and transplantation of cell subsets, including adult stem cells and platelets, which are specifically used to repair organs in regenerative medicine. The system includes a set of components consisting of a disposable sterile fluid delivery element, which is pre-connected, or includes sterile connectors, or is suitable for interconnection in a sterile manner. The subassembly usually consists of three sets of disposable sterile components: a set of collection device, a set of treatment device and a set of transplantation device. Three sets of devices include bubble-cap packages on supports such as trays, which have a compartment for receiving interconnected sets of components. The components include extraction devices, such as needles for piercing bone or blood vessels, for extracting bone marrow or other cell subsets from patients.

In one example, Chinese Patent Publication CN107635668A presents a device for processing and separating biological fluids into components, including a hollow centrifugal processing chamber with an inlet/outlet head and an axially moving piston. The inlet/outlet head has two separate inlets/outlets, such as an axial inlet and a lateral outlet. The processing chamber (1) is equipped with an internal diversion device, enabling the device to operate in a continuous processing mode, in which the biological fluid pending to be processed is continuously imported by the axial inlet, while the processed components that pass through the chamber's lateral outlet are continuously removed. However, the existing techniques mentioned above can only complete some steps of cell preparation or can only be used for cell separation. They have single function and complex structure, and need to be further optimized.

Therefore, a heretofore unaddressed need exists in the art to address the aforementioned deficiencies and inadequacies.

In summary, the present application has broad application prospects and great market value to provide a device that can complete the preparation of immune cells, reduce the pollution caused by multi-equipment operation, reduce the frequency of manual operation, and improve the success rate of cell preparation.

SUMMARY

In view of the shortcomings of the existing technology and the actual requirements, the present disclosure provides a device for cells preparation, which includes an automatic blood component separator for cell cultivation and preparation, uses a weight sensor to have the weight, and adds a gas intake device and a liquid sensor. By optimizing the connection relationship of each device in the whole equipment, simplifying the operation process of the equipment, coordinating each step of the device, improving the success rate of cell preparation, it has broad application prospects and large market value.

To achieve this goal, the disclosure has the following technical features:

Firstly, the disclosure provides an apparatus for processing a blood sample includes a sample introduction device, a centrifugal device, and a first collection device. However, an ordinary skill in the art understands that the present disclosure is not limited to the blood sample itself. Any biological fluid such as blood, peripheral blood, buffy-coat, bone marrow and cord blood can be utilized in the apparatus of the present disclosure. The blood sample is utilized as an exemplary illustration of the present disclosure.

the sample introduction device is configured to provide a blood sample to be separated;

the centrifugation device is used for extracting the blood sample from the sample introduction device and separating at least one component from the blood sample under centrifugal force, and further for pushing the at least one separated component to the first collection device;

the pipeline between the sample introduction device and the centrifugal device is provided with a first liquid sensor, and the pipeline between the centrifugal device and the first collection device is provided with a second liquid sensor, wherein the first liquid sensor is configured to detect a color of a sample flowing through the pipeline when the centrifugal device extracts the blood sample from the sample introduction device;

the second liquid sensor is configured to detect a color of the at least one separated component flowing through the pipeline when the centrifugal device pushes the at least one separated component to the first collection device.

Preferably, the apparatus further includes an air extracting/compressor device coupled to the centrifugal device, wherein the centrifugal device extracts the blood sample or pushes the at least one separated component under the action of the air extracting/compressor device.

Preferably, the centrifugal device includes a piston, and the centrifugal device uses the piston to extract the blood sample or push the at least one separated component.

Preferably, the sample introduction device is connected with a first weight sensor; and the apparatus calculates the weight of the blood sample drawn by the centrifugal device by the signal of the first weight sensor and the parameters of the pipeline through which the blood sample flows into the centrifugal device.

Preferably, the collection device is connected with a second weight sensor; the apparatus calculates the weight of the at least one separated component pushed by the centrifugal device by the signal of the second weight sensor and the parameters of the pipeline through which the at least one separated component flows into the first collection device.

Preferably, the centrifugal device includes a temperature control module to control the temperature inside thereof.

Preferably, the apparatus further includes a gas device coupled to the centrifugal device; the gas device provides a gas environment favorable for cell culture to the centrifugal device.

Preferably, the apparatus further includes a second collection device; along the pipeline, it is sequentially provided with the second liquid sensor, the first collection device and the second collection device, wherein a first three-way valve is disposed between the first collection device and the second collection device.

Preferably, the apparatus further includes a third collection device connected with a third weight sensor; and a second three-way valve is disposed between the first liquid sensor and the second liquid sensor along the pipeline, and the second three-way valve is connected to the third collection device. However, an ordinary skill in the art understands that the present disclosure is not only limited to the facts that the first valve and the second valve are of three-way valves.

The first valve can include, for example, a pinch valve. The three-way valve is utilized as an exemplary illustration of the present disclosure. In other words, in the present disclosure, any three-way valve, for example, can include a pinch vale. Further, the present disclosure may also include a combination of the three-way valve and other types of valves. For example, the first valve is a three-way valve and the second three-way valve is a pinch valve.

Preferably, the apparatus further includes a magnetic device having a permanent magnet or an electromagnet; and the magnetic device is used for applying a fixed or variable magnetic force to a magnetic substance flowing through the pipeline, wherein the linear distance between the magnetic device and the pipeline is variable when a variable magnetic force is applied.

Preferably, a filter for filtering blood clots is provided between the sample introduction device and the first liquid sensor.

Preferably, along the pipeline, a third three-way valve is disposed between the second liquid sensor and the first collection device and the third three-way valve is connected with a device for supplying normal saline, wherein the device for supplying normal saline is connected with a fourth weight sensor.

Preferably, along the pipeline, a fourth three-way valve is disposed between the second liquid sensor and the first collection device, and the fourth three-way valve is connected with a device for supplying culture medium, wherein the device for supplying culture medium is connected with a fifth weight sensor.

Preferably, the first liquid sensor or the second liquid sensor includes a light emitting end and a light receiving end, and operates by emitting and receiving light of different wavelengths, and the first liquid sensor or the second liquid sensor is further configured to determine whether the pipeline reaches a certain degree of cleanliness.

Preferably, the centrifugal device is connected with a sixth weight sensor.

Preferably, the first collection device is further connected with a sample acquisition device.

Preferably, the apparatus further includes a human interface device, and by the use of the human-machine interface device, or by the use of program module in the human-machine interface device, the apparatus interactively or automatically control any of the following: the extraction or pushing action of the centrifugal device, and the action of various valves disposed along the pipeline, wherein any of the various valves is a rotatable three-way valve, and for each rotatable three-way valve, a clamping structure is provided to clamp the rotatable three-way valve and the clamping structure is rotated by the motor to drive the rotatable three-way valve to rotate, so as to: control the switching of the rotatable three-way valve between opening and closing by the clockwise and counter-clockwise motion of the motor, and control the flow rate of liquid by the duration when the motor opens the rotatable three-way valve.

Preferably, the parameters of the pipeline include any one or any combination of the following: length, diameter, and volume of the pipeline.

Preferably, the first collection device or the second collection device is a collection bag, wherein the first collection device is capable of adding immunomagnetic beads and the immunomagnetic beads can be drawn by the centrifugal device.

Preferably, the third collection device is a device for accommodating the medium or waste liquid, and is capable of recovering the magnetic beads pushed by the centrifugal device.

Alternatively, the disclosure provides a device for preparing cells, which includes a sample injection device, a collecting device, a fluid supplementation device, a centrifugal cultivation device, a liquid sensor device, a gas exchange device, a weighing subassembly device and a magnetic control device.

The liquid sensor device includes a first liquid sensor and a second liquid sensor, wherein the first liquid sensor is connected with the sample injection device and the second liquid sensor is connected with the centrifugal cultivation device.

The weighing subassembly device includes a weight sensor, which is respectively installed on the sample injection device, the collecting device, the centrifugal cultivation device and the fluid supplementation device.

The sample injection device, the centrifugal cultivation device, the gas exchange device, the magnetic control device, the fluid supplementation device and the collection device are connected in turn.

The process of cell therapy is described as follows: generally, it can be divided into the following steps: peripheral blood collection→peripheral blood mononuclear cells (PBMC) separation→specific lymphocyte populations separation→cells activation→cells incubation→virus transfection→cells amplification→cell preparations after cells washing→cells reinfusion. Peripheral blood collection and cell reinfusion are performed manually. The intermediate "peripheral blood mononuclear cells (PBMC) separation→specific lymphocyte populations separation→cells activation→cells incubation→virus transfection→cells amplification→cell preparations after cells washing" is the process of cell preparation. The disclosure mainly solves the closed automatic processing technology of "PBMC cell separation→specific population cell separation" two steps.

In the disclosure, in order to achieve more efficient preparation of cells, the inventor first improves the apparatus to be an automatic blood separator. In order to integrate the multi-step preparation of immune cells into a single device, a gas intake device and a liquid color sensor are added, and a weight sensor is utilized to reduce the cost of the machine. According to the equipment, a set of methods have been developed to study and practice the whole process of cell preparation repeatedly, overcome the difficult problems that multiple units cannot be used together, optimize the connection relationship and order of use of the device, avoid the pollution of multi-step operation and reduce the labor cost, and smoothly realize the concise and high-efficient cell preparation process.

In the present disclosure, the weight sensor is utilized and is installed separately on the sample injection device, collection device, centrifugal cultivation device and fluid supplementation device, and feedback control system is realized by weight sensing detection of consumables such as collection bags or sample bags. The gas intake device regulates gas exchange and flow between the centrifugal cultivation device and the pipeline. The liquid sensor device is respectively installed in the sample injection device and the centrifugal cultivation device to monitor and control the key components of the equipment and the main steps of the method. Finally, it can achieve the goal of high-efficient and concise preparation of cells.

Preferably, the sample injection device comprises a blood bag connector 1, a blood clot filter 31 and a first pipe clamp 8.

Preferably, the blood bag connector 1, the blood clot filter 31 and the first pipe clamp 8 are sequentially connected.

Preferably, the sample injection device is connected with the first valve 15 through the first liquid sensor 4.

Preferably, the centrifugal culture device comprises a lymphatic separation liquid/waste liquid bag 5, a first liquid filter 21, a second pipe clamp 11, a first valve 15, a first injection port 22, a second injection port 23, a temperature control module 48, a dynamic sealing module 27, a centrifugal bucket 29, a piston 28 and a first gas filter 30.

Preferably, the first liquid filter (21), the lymphatic separation liquid/waste liquid bag (5), the second pipe clamp (11), the first valve (15), the second liquid sensor (45), the first injection port (22), the second injection port (23), the dynamic sealing module (27), the centrifugal barrel (29) and the first gas filter (30) are connected in turn.

Preferably, the centrifugal barrel (29) contains a piston (28) inside.

Preferably, the centrifugal barrel (29) externally contains a temperature control module (48).

Preferably, the device also contains a centrifugal driving device and a pneumatic device.

Preferably, the centrifugal driving device comprises an electric rotating motor (49) and a transmission device (50).

Preferably, the pneumatic device comprises a first gas pressure detector (43) and a pneumatic control device (51).

Preferably, the centrifugal driving device is connected with a centrifugal cultivation device.

Preferably, the pneumatic device is connected with a centrifugal cultivation device.

Preferably, the pneumatic device comprises a first gas pressure detector 43 and a gas pressure control device 51.

Preferably, the gas exchange device comprises a second gas pressure detector (42), a fifth valve (46) and a gas route joint (61);

Preferably, the fifth valve (46), the second gas pressure detector (42) and the gas route joint (51) are connected in turn.

Preferably, the fluid supplementation device comprises a normal saline connector (2-3), a cultivation medium bag (4), a third pipe clamp (9), a third valve (16), a fourth valve (17), a fourth pipe clamp (10) and a second liquid filter (20).

Preferably, the normal saline connector (2-3) is connected sequentially with the fourth valve (17) through the third pipe clamp (9).

Preferably, the second liquid filter (20), the medium bag (4), the fourth pipe clamp (10) and the fourth valve (17) are connected in turn, and the third valve (16) and the fourth valve (17) are connected in turn.

Preferably, the collection device comprises a sixth valve (18), a fifth pipe clamp (12), a sixth pipe clamp (13), a seventh pipe clamp (14), a first collection bag (6), a second collection bag (7), a third injection port (24), a fourth injection port (25) and a sampling bag (26).

Preferably, the sampling bag (26), the fifth pipe clamp (12), the first collecting bag (6), and the sixth pipe clamp (13) and the sixth valve (18) are connected in sequence.

Preferably, the second collection bag (7) is connected with the sixth valve (18) through the seventh pipe clamp (14).

Preferably, the first collection bag (6) is also connected with a third injection port (24) and a fourth injection port (25).

Preferably, the magnetic control device comprises a controllable magnet (47).

Preferably, the controllable magnets (47) include permanent magnets or non-permanent magnets.

Preferably, the valves include any or at least two combinations of solenoid valves, pinch valves or rotary valves.

Preferably, the device also includes a shell structure.

Preferably, the shell structure is embedded with a valve rotating mechanism (52-54), a centrifugal barrel clamp (62), a first liquid sensor (44), a second liquid sensor (45), a gas path joint (61) and a controllable magnet (47).

Preferably, the shell structure is distributed with 2-10 weight sensors, such as 2, 3, 4, 5, 6, 7, 8, 9 or 10 weight sensors.

Preferably, the shell device also includes a human-machine interface (56).

Thirdly, the disclosure provides a method for preparing cells using the equipment described in the first part, which comprises the following steps:

(1) gradient centrifugation is used to centrifuge in the centrifugal cultivation device. The liquid flow is regulated by liquid sensor device, centrifugal cultivation device and weighing subassembly device, and the cells in the sample are separated into collection device.

(2) the antibody magnetic beads larger than or equal to 1 micron in diameter are added to the cells collected in step (1) and transferred to the centrifugal cultivation device. The target cells are separated by the magnetic control device, and then the cells are collected by the collection device. Step (2) is that the collected cells are not only limited to further cell activation and can be used to prepare immune cells.

Preferably, the method also includes initialization steps before step (1). The initialization steps include preparing samples, connecting consumables, and self checking.

Preferably, the consumables include a blood sample bag (35), a lymphatic separation liquid/waste liquid bag (5), a first collection bag (6), a second collection bag (7), a normal saline bag (33-34), a medium bag (4) and a centrifugal barrel (29).

The detailed operation of initialization is as follows:

sample preparation: clamp all the pipes in the pipeline, close the pipeline, inject the culture medium and lymphatic separation liquid into the designated storage bag through filters, connect the blood sample and normal saline separately through the connecting parts of consumables.

connection of consumables: hang blood samples, saline solution, lymphatic separation liquid and the collecting bag on the machine according to the order, connect the three-way valve with the rotary mechanism of the three-way valve of the machine, connect and fix the centrifugal barrel with the equipment, connect the gas filter with the equipment, and clip the pipeline into the first liquid sensor and the second liquid sensor.

self-inspection: loosen the clamp in the pipeline (except for the clamp in the sample collection bag), detect the detection pipeline by the first liquid sensor and the second liquid sensor, and test the leak-proofness of the pipeline by the pneumatic control device, the first air pressure sensor and the second air pressure sensor.

Among them, the operation of step (1) is that:

peripheral blood mononuclear cells (PBMC) are separated by gradient centrifugation of lymphatic separating fluid (Ficoll). The steps are as follows: rotating centrifugal barrel, injecting Ficoll into centrifugal barrel, and slow inject samples (peripheral blood or apheresis component) into centrifugal barrel. Under centrifugation, red blood cells penetrate the Ficoll and PBMC cells are on the Ficoll to achieve separation effect. By adding air into the barrel, the centrifugal distance can be increased, and thus the centrifugal time can be reduced. Then, the different components are separated by piston push-up cooperated with the second liquid sensor. Some plasma, PBMC cells and some Ficoll are collected and transferred into the first collection bag. Some Ficoll and red blood cells are transferred into the sample bag. The PBMC cells are centrifugally rinsed with normal saline, and then collected or prepared directly for the follow steps.

Among them, the detailed operation of step (1) is that:

by controlling the piston, the blood sample is slowly extracted to the first liquid sensor, then stopping the extraction. The Ficoll is pumped into the centrifugal barrel while the blood sample is not in the centrifugal barrel yet. The centrifugation is started and then the blood sample is pumped into the centrifugal barrel. The liquid will be divided into plasma layer, PBMC cell layer, Ficoll and red blood cell layer from inside to outside of the centrifugal barrel. The liquid in the centrifugal barrel will be pushed out slowly by the piston. Under the centrifugal action, the liquid will be pushed out from inside to outside in turn. The liquid passing through is detected and analyzed by the second liquid sensor, and different liquid components are collected into different collection bags with the rotary three-way valve and the pipeline. The first half of serum is pushed into the original blood sample bag, and the second half of serum, together with the PBMC cell layer and the first half of Ficoll, is pushed into the first collection bag. The latter part of the lymph fluid and the red blood cells are pushed to the waste bag or blood sample bag.

Preferably, the method includes a step of flushing the pipeline after step (1) and before step (2).

Preferably, the steps of the flushing pipeline are as follows: the normal saline in the fluid supplementation device is pumped into the centrifugal barrel (29) and discharged into the Ficoll bag 39.

Preferably, the number of the flushing pipes is 1-6 times. The operation of the cleaning pipeline is as follows: the centrifugal barrel pipeline is connected with the normal saline pipeline. The normal saline is pumped into the centrifugal barrel through the piston, and then the normal saline is discharged into the Ficoll bag/waste liquid bag. The purpose of thorough cleaning can be achieved by repeated these steps.

Among them, the operation of step (2) is that: in the first collection bag, the antibody magnetic beads are added to make the antibody magnetic beads fully mixed with the cell fluid, and recycled to the centrifugal barrel; the liquid in the barrel is cleaned, and is replaced by the culture medium, and then the liquid is incubated for a period of time. (The antibody beads will bind to the target cells that need to be screened, so that the cells can be adsorbed by a magnet and the rest of the unwanted cells can be discharged.) The operation further includes: activating the magnet and letting the cell liquid pass through the magnet (which can be controlled by the electromagnet or the permanent magnet can be activated and eliminated by moving). The target cell will be adsorbed by the magnet, and other unwanted cell liquid will be discharged into the waste liquid bag, then the part adsorbed by the magnet will be flushed and discharged into the waste liquid bag. Finally, the magnet is removed and the target cells are collected with the medium.

Among them, the detailed operation of step (2) is that: manual operation adds magnetic bead antibody in the first collection bag and fully mixes it. The cell liquid in the first collection bag is pumped back into the centrifugal barrel, diluted by normal saline, and centrifuged. The liquid in the barrel is slowly pushed out to the waste liquid bag, leaving a small amount of liquid in the barrel. The following steps are performed to repeat the above washing steps several times (e.g. 2 times), connect the culture medium and push it into the barrel. stop centrifugation, still incubate for a period of time (e.g. 15 minutes), and rotate the centrifugal barrel several times (mixing mode) at intervals (e.g. 5 minutes).

The controllable magnet is activated; the cell liquid in the centrifugal barrel is discharged into the first collection bag; and then pumped back into the barrel. The liquid in the barrel is connected with the waste liquid bag; and all the liquid is discharged into the waste liquid bag. The following steps are performed to connect the centrifugal barrel with the culture medium bag, put the culture medium into the barrel and drain it again into the waste liquid bag, remove the activated magnet, connect the centrifugal barrel and the culture medium bag, put the culture medium together with the cells sorted by magnetic beads in the pipeline into the barrel, and then drain the cell liquid in the barrel into the first collection bag.

Preferably, the method also includes the operation of removing the magnetic beads from the hatched cells.

Preferably, the operation of removing magnetic beads is as follows: adding magnetic beads to the cells obtained in step (2) to remove enzymes, mixing and incubating in a centrifugal cultivation device, and removing magnetic beads through a magnet control device.

The steps for removing magnetic beads are as follows:

when incubation is completed, the excessive gas is discharged; magnetic beads are added to the centrifugal barrel to remove enzymes, mixed with cells, and incubated for a period of time (e.g. 15-20 minutes). The following steps are performed to activate the magnet, connect the centrifugal barrel with the second collection bag, and push the cells to the second collection bag. In the process, the magnetic beads will be attracted by the magnet, and the cells will pass through directly. In order to separate the magnetic beads from the cell, the magnet is removed and the magnetic beads are flushed into the waste liquid bag.

As a preferred technical scheme, a method for preparing cells employing the device comprises the following steps:

(1) samples are prepared, and consumables are connected and self-checked. The consumables include the blood sample bag 35, the Ficoll/waste liquid bag 5, the first collection bag 6, the second collection bag 7, the saline bag 33-34, the culture medium bag 4 and the centrifugal barrel 29.

The gradient centrifugation method is used to centrifuge in the centrifugal cultivation device. The liquid flow is regulated by the liquid sensor device, weighing device and valve device, and the cells in the sample are separated into the collection device.

The normal saline in the rehydration device is pumped into the centrifugal barrel 29, and then discharged into the Ficoll/waste liquid bag 39, and these steps are repeated for many times.

(2) adding antibody magnetic beads larger than or equal to 1 micron in diameter to the cells collected in step (1) and transferring them to the centrifugal cultivation device. The target cells are separated by the magnet control device, and then the enzymes are removed by adding magnetic beads. After mixed incubation in the centrifugal cultivation device, the magnetic beads are removed by the magnet control device, and the cells are collected by the collection device.

1. The Consumable System

The system consists of a set of liquid storage bags and a centrifugal container. There are pistons in the centrifugal container. The piston can move up and down. It can inhale or push into the liquid to achieve variable centrifugal volume. With the switching of the direction of the pipeline, the centrifugal product can be collected into the corresponding liquid storage bag. There are four rotary three-way valves, which can realize the flow direction of the liquid in the pipeline of consumables system by changing the direction of the valve.

2. Cell Preparation System (Machine)

① The system contains a set of consumable system.

② The system includes a set of centrifugal driving device which drives the rotation of consumables centrifugal vessel and up and down of piston. The device includes motor (driving centrifugal vessel rotation), air pump, solenoid valve, dynamic sealing structure (blowing or pumping gas to centrifugal vessel to realize up and down of piston), and the second air pressure sensor (check the pressure of the centrifugal container and check the limit position of the piston).

(3) The system includes a set of temperature control module, which can ensure the centrifugal vessel to work at a certain temperature (such as 37 degrees). The device has the functions of heating, insulation, temperature detection and temperature compensation.

(4) The system includes two liquid color sensor devices. The device can detect the color of liquid flowing through the device, cooperate with rotating three-way valve, and can separate different color liquid into different collection bags.

(5) The system includes four driving devices of rotary three-way valves, which can be used to drive rotary three-way valves, or other solenoid valves can be used to replace the device. The switch of valves can change the direction of consumables pipelines.

(6) The system includes a gas exchange device which can feed gas into the pipeline consumables system and detect the sealing of the pipeline consumables system. There are pressure sensors (which can detect pipeline pressure), pinch valves (which can also be replaced by other solenoid valves and rotary valves) to control the opening and closing of the gas into the consumables pipeline.

(7) The system consists of a set of weighing subassembly devices. Each collection bag is fixed on a device with weighing function. The weighing device can accurately measure the weight of each collection bag and ensure the entering and pushing out volume accuracy of the centrifugal container.

(8) The system includes a magnet control device. The magnet of the device has movable function. When the magnetic beads of the consumables system need to be absorbed, the magnet of the device will move to the position near the consumables pipeline. On the contrary, it will be far away from the pipeline. The controllable magnet can also be an electromagnet. The power "on" is magnetic, with the function of adsorption magnetic beads, power "off" is not magnetic, that cannot absorb magnetic beads.

3. Control Principle System (1) The gas pump inflates the centrifugal vessel, and the controller reads the pressure of the second air pressure sensor to check whether the centrifugal vessel is leaking, and the next step is output by the human-computer interface.

(2) The gas pump extracts gas from the centrifugal vessel, and the controller reads the pressure of the first air pressure sensor to detect whether the consumables pipeline is leaking or not, and the next step is output from the human-computer interface.

(3) The controller reads the weight of the storage bag of consumables. According to the requirements, the controller controls the rotary three-way valves to change the direction of the pipeline. The gas pump drives the piston of the centrifugal container and pumps a certain weight of liquid into the centrifugal container. Or from a centrifugal container to a certain bag, a certain amount of liquid is released.

4. The controller reads the temperature of the temperature control module in real time and controls the on-off of the heating module.

5. The controller controls the movement of controllable magnet (or on-off power) according to the experimental process to absorb magnetic beads of pipeline.

Compared with the prior technology and the equipment of a single process, the disclosure has the following beneficial effects: the present disclosure realizes multiple processes in one device, which can reduce the number of manual operations and the pollution and human errors caused by cell transfer in different devices. The method of the present disclosure optimizes the operation process. The method provided by the disclosure optimizes the operation process, reduces the requirements for personnel operation, reduces the production cost, integrates the process of PBMC separation and magnetic bead separation, makes the cell preparation process more intelligent and automated, makes the operation simpler, improves the success rate of cell preparation. It has broad application prospects and huge market value.

BRIEF DESCRIPTION OF THE DRAWINGS

The accompanying drawings illustrate one or more embodiments of the present disclosure and, together with the written description, serve to explain the principles of the disclosure. Wherever possible, the same reference numbers are used throughout the drawings to refer to the same or like elements of an embodiment.

Figure 9:
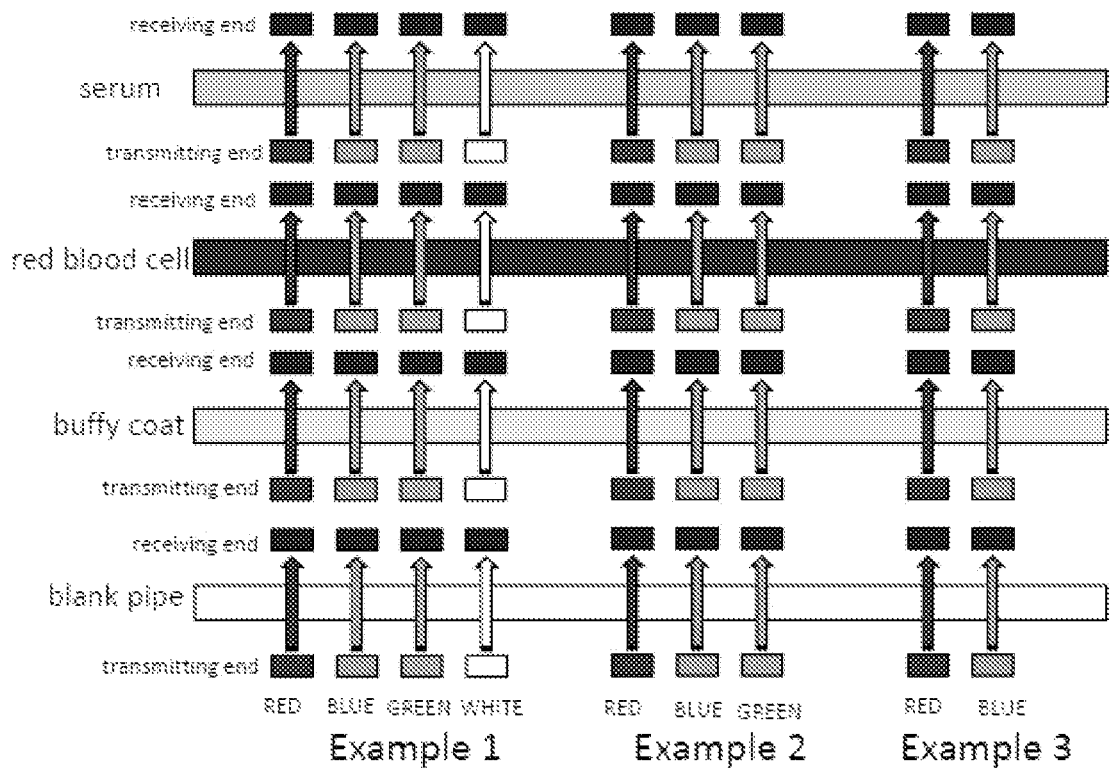
FIG. 9 shows liquid sensor to detect color information of different components, and different examples of sensor arrangement, wherein in example 1 of FIG. 9, the light emitting end has RGBW (Red, Green, Blue, and White) emitting units from left to right.

in example 2 of FIG. 9, the light emitting end has RGB (Red, Blue, and Green) emitting units from left to right; in example 3 of FIG. 9, the light emitting end has RG (Red and Blue) emitting units from left to right; and in examples 1 to 3 of FIG. 9, the light receiving end can be same from left to right.

Figure 10:
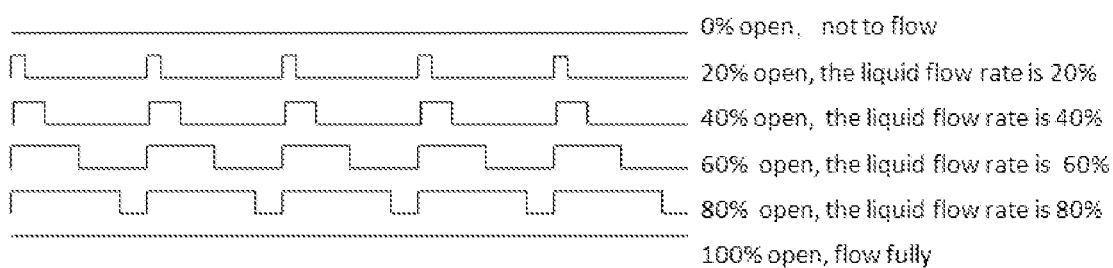

FIG. 10 describes the specific control of the flow rate of the liquid.

DETAILED DESCRIPTION

The present disclosure will now be described more fully hereinafter with reference to the accompanying drawings, in which exemplary embodiments of the present disclosure are shown. The present disclosure may, however, be embodied in many different forms and should not be construed as limited to the embodiments set forth herein. Rather, these embodiments are provided so that this disclosure is thorough and complete, and will fully convey the scope of the disclosure to those skilled in the art. Like reference numerals refer to like elements throughout.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It is appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the disclosure or of any exemplified term. Likewise, the disclosure is not limited to various embodiments given in this specification.

It is understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It is understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the present disclosure.

It is understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It is also appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It is further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It is understood that relative terms are intended to encompass different orientations of the device in addition to the orientation shown in the figures. For example, if the device in one of the figures is turned over, elements described as being on the "lower" side of other elements will then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements will then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the present disclosure belongs. It is further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the terms "comprise" or "comprising," "include" or "including," "carry" or "carrying," "has/have" or "having," "contain" or "containing," "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. It should be understood that one or more steps within a method may be executed in different order (or concurrently) without altering the principles of the disclosure.

Embodiments of the disclosure are illustrated in detail hereinafter with reference to accompanying drawings. It should be understood that specific embodiments described herein are merely intended to explain the disclosure, but not intended to limit the disclosure.

In order to further elaborate the technical means adopted by the present disclosure and its effect, the technical scheme of the present disclosure is further illustrated in connection with the drawings and through specific mode of execution, but the present disclosure is not limited to the scope of the implementation examples.

Case 1: Equipment Assembly

The present example provides a device, which includes a sample injection device, a collection device, a fluid supplementation device, a centrifugal cultivation device, a liquid sensor device, a gas exchange device, a weighing subassembly device and a magnet control device.

The liquid sensor device includes a first liquid sensor and a second liquid sensor, wherein the first liquid sensor is connected with the sample injection device and the second liquid sensor is connected with the centrifugal cultivation device; the weighing subassembly device comprises a weight sensor, which is respectively installed in the sample injection device, the collection device, the centrifugal cultivation device and a fluid supplementation device. A sample injection device, a centrifugal cultivation device, a gas exchange device, a magnet control device, a fluid supplementation device and a collection device are connected in turn. The sample injection device comprises a blood bag connector (1), a blood clot filter (31) and a first pipe clamp (8); the blood bag connector (1), the blood clot filter (31) and the first pipe clamp (8) are sequentially connected. The sample injection device is connected with the first valve (15) through the first liquid sensor (44). The centrifugal cultivation device comprises a Ficoll/waste liquid bag (5) and a first liquid filter (21), the second pipe clamp (11), the first valve (15), the first injection port (22), the second injection port (23), the temperature control module (48), the dynamic sealing module (27), the centrifugal barrel (29), a piston (28) and the first gas filter (30). The first liquid filter (21), the Ficoll/waste liquid bag (5), the second pipe clamp (11), the first valve (15), the second liquid sensor (45), the first injection port (22), the second injection port (23), the dynamic sealing module (27), the centrifugal barrel (29) and the first gas filter (30) are connected in turn. The centrifugal barrel (29) contains a piston (28) inside. The centrifugal barrel (29) externally contains a temperature control module (48). The device also contains a centrifugal driving device and a pneumatic device. The centrifugal driving device comprises an electric rotating motor (49) and a transmission device (50). The pneumatic device comprises a first gas pressure detector (43) and a pneumatic control device (51). The centrifugal driving device is connected with a centrifugal cultivation device. The pneumatic device is connected with a centrifugal cultivation device. The gas exchange device includes a second gas pressure detector (42), a fifth valve (46) and a gas route joint (61). The fifth valve (46), the second gas pressure detector (42) and the gas route joint (51) are connected in turn. The fluid supplementation device comprises a normal saline connector (2-3), a cultivation medium bag (4), a third pipe clamp (9), a third valve (16), a fourth valve (17), a fourth pipe clamp (10) and a second liquid filter (20). The normal saline connector (2-3) is connected sequentially with the fourth valve (17) through the third pipe clamp (9). The second liquid filter (20), the medium bag (4), the fourth pipe clamp (10) and the fourth valve (17) are connected in turn, and the third valve (16) and the fourth valve (17) are connected in turn. The collection device comprises a sixth valve (18), a fifth pipe clamp (12), a sixth pipe clamp (13), a seventh pipe clamp (14), a first collection bag (6), a second collection bag (7), a third injection port (24), a fourth injection port (25) and a sampling bag (26). The sampling bag (26), the fifth pipe clamp (12), the first collecting bag (6), and the sixth pipe clamp (13) and the sixth valve (18) are connected in sequence. The second collection bag (7) is connected with the sixth valve (18) through the seventh pipe clamp (14). The first collection bag (6) is also connected with a third injection port (24) and a fourth injection port (25). The magnetic control device comprises a controllable magnet (47). The controllable magnets (47) are permanent magnets. The valve is a rotating three-way valve. The device includes a shell structure. The shell structure is embedded with a valve rotating mechanism (52-54), a centrifugal barrel clamp (62), a first liquid sensor (44), a second liquid sensor (45), a gas path joint (61) and a controllable magnet (47). There is a weight sensor near the upper side on the left side of the shell structure, and two weight sensors near the upper side on the right side. A vertical pole is erected in the middle of the rear side of the shell structure, a flat cylinder is supported at the top of the vertical pole, and four weight sensors are evenly distributed on the side of the cylinder. The shell device also includes a human-computer interface 56, which is located on the front side of the shell structure.

The above devices are connected in the order of connection and location shown in FIG. 1-5, and assembled into the equipment for cell preparation.

Case 2 Preparation of Cells

The following steps are taken to prepare cells:

(1) preparing a sample of 100 mL blood, connecting the consumables and making self-examination. The consumables include the blood sample bag 35, the Ficoll/waste liquid bag 5, the first collection bag 6, the second collection bag 7, the normal saline bag 33-34, the culture medium bag 4 and the centrifugal barrel 29.

Gradient centrifugation is used to centrifuge in the centrifugal cultivation device. The liquid flow is regulated by liquid sensor device, centrifugal cultivation device and weighing subassembly device, and the cells in the sample are separated into collection device. The normal saline in the fluid supplementation device is pumped into the centrifugal barrel 29, and then discharged into the Ficoll/waste liquid bag 39, and the steps are repeated many times.

(2) adding antibody magnetic beads to the cells collected in step (1) and transferring them to the centrifugal cultivation device. The target cells are separated by the magnet control device, and then the enzymes are removed by adding magnetic beads. After mixed incubation in the centrifugal cultivation device, the magnetic beads are removed by the magnet control device, and then the cells are collected by the collection device.

The detailed procedures are as follows:

sample preparation: clamp all the pipes in the pipeline, close the pipeline, inject the culture medium and Ficoll into the designated storage bag through filters, connect the blood sample and normal saline separately through the connecting parts of consumables.

connection of consumables: hang 100 mL blood samples, saline solution, Ficoll and the collecting bag on the machine according to the order, connect the three-way valve with the rotary mechanism of the three-way valve of the machine, connect and fix the centrifugal barrel with the equipment, connect the gas filter with the equipment, and clip the pipeline into the first liquid sensor and the second liquid sensor.

self-inspection: loosen the clamp in the pipeline (except for the clamp in the sample collection bag), detect the detection pipeline by the first liquid sensor1 and the second liquid sensor2, and test the leak-proofness of the pipeline by the pneumatic control device, the first air pressure sensor and the second air pressure sensor.

Pbmc Separation:

by controlling the piston, the blood sample is slowly extracted to the first liquid sensor; then the extraction is stopped. The Ficoll is pumped into the centrifugal barrel while the blood sample is not in the centrifugal barrel yet. The centrifugation is started and then the blood sample is pumped into the centrifugal barrel The liquid will be divided into plasma layer, PBMC cell layer, Ficoll layer and red blood cell layer from inside to outside of the centrifugal barrel. The liquid in the centrifugal barrel is pushed out slowly by piston. Under centrifugal action, the liquid will be pushed out from the inside to the outside in turn. The liquid passed through will be detected and analyzed by the second liquid sensor, and different liquid components will be collected into different collection bags with rotary three-way valve and pipeline. The first half of the serum is pushed into the original blood sample bag, the second half of the serum, together with the PBMC cell layer and the first half of the Ficoll, is pushed into the first collection bag, and the second half of the Ficoll and the red blood cells are pushed into the waste liquid bag or the blood sample bag.

Flushing Pipeline and Centrifuge Barrel:

the centrifugal barrel pipeline is connected with the normal saline pipeline. The normal saline is pumped into the centrifugal barrel through the piston, and then the normal saline is discharged into the Ficoll bag/waste liquid bag. The purpose of thorough cleaning can be achieved as the steps are repeated above.

Magnetic Beads Sorting:

manual operation adds CD3+CD28 magnetic bead antibody in the first collection bag and fully mixes it. The cell liquid in the first collection bag is pumped back into the centrifugal barrel, diluted by normal saline, and centrifuged. The liquid in the barrel is slowly pushed out to the waste liquid bag, leaving a small amount of liquid in the barrel. Repeat the above washing steps 2 times. The following steps are performed to: connect the culture medium and push it into the barrel, stop centrifugation, still incubate for 15 minutes, and rotate the centrifugal barrel several times (mixing mode) at an interval of 5 minutes.

The controllable magnet is activated; the cell liquid in the centrifugal barrel is discharged into the first collection bag; and then pumped back into the barrel. The liquid in the barrel is connected with the waste liquid bag, and all the liquid is discharged into the waste liquid bag. The following steps are performed to connect the centrifugal barrel with the culture medium bag, put the culture medium into the barrel and drain it again into the waste liquid bag, remove the activated magnet, connect the centrifugal barrel and the culture medium bag, put the culture medium together with the cells sorted by magnetic beads in the pipeline into the barrel, and then drain the cell liquid in the barrel into the first collection bag.

The magnetic beads are added to the centrifugal barrel to remove enzymes, then incubate for 20 minutes, activate the magnet, connect the centrifugal barrel with the second collection bag and push the cells to the second collection bag. In the process, the magnetic beads are attracted by the magnet, and the cells will pass directly through, thus for achieving the goal of separating the magnetic beads from the cells.

The magnet is deactivated and connected with the normal saline bag and the centrifugal barrel. The magnetic beads in the pipeline are pumped into the centrifugal barrel through the normal saline. Then the centrifugal barrel is connected with the waste liquid bag, and the magnetic beads are discharged into the waste liquid bag. Finally, the cells are collected by a collection device.

Experimental Detection

The results of separation and sorting of 100 mL blood sample are as follows:

1. The separation of PBMC:

a. In one example, the results of separation by the present disclosure may include obtaining 1E8 PBMC from every 100 mL whole blood sample, and the highest sample can be more than 2.5 E8 PBMC cells per 100 mL whole blood. The results may show an exemplary illustration of the present disclosure; and may not be limited to description in the present disclosure.

b. The viability of PBMC is greater than 90%.

c. The depletion rate of red blood cell is greater than 99%.

2. CD3 cell sorting a. CD3+ cell sorting rate is greater than 75%.

b. The purity of CD3+ cells is greater than 95%.

Figure 1:
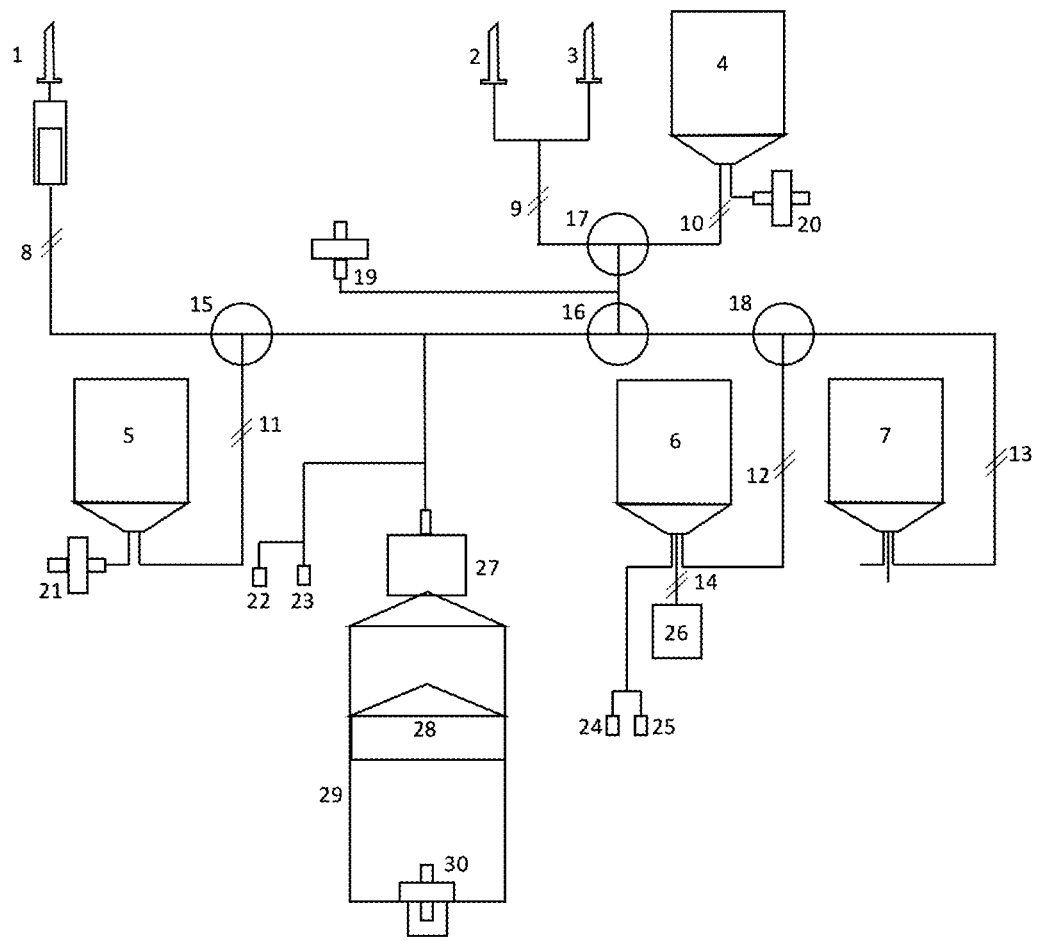
FIG. 1 is a schematic diagram of the air consumable material system of the disclosure.
Figure 2:
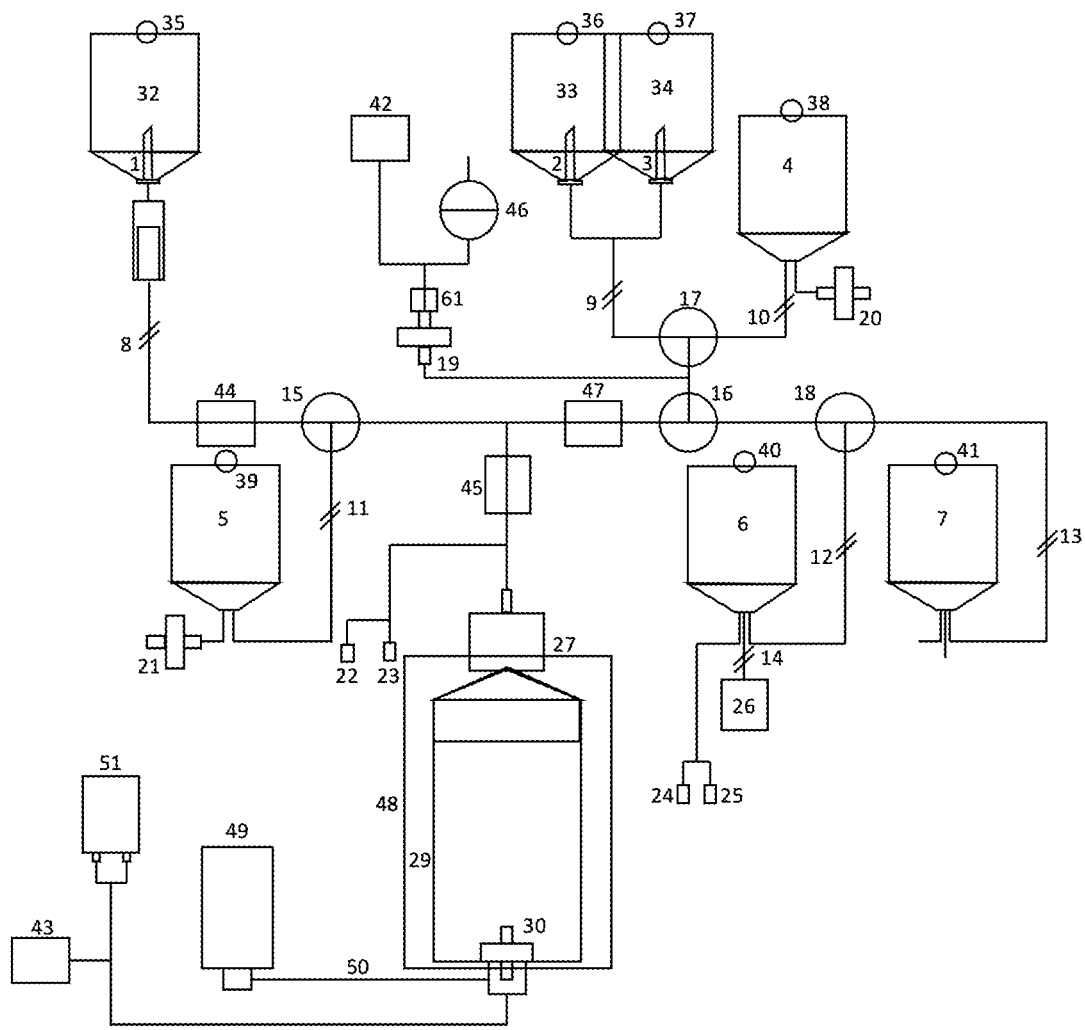
FIG. 2 is a schematic diagram of system connection and a cell preparation system.
Figure 3:
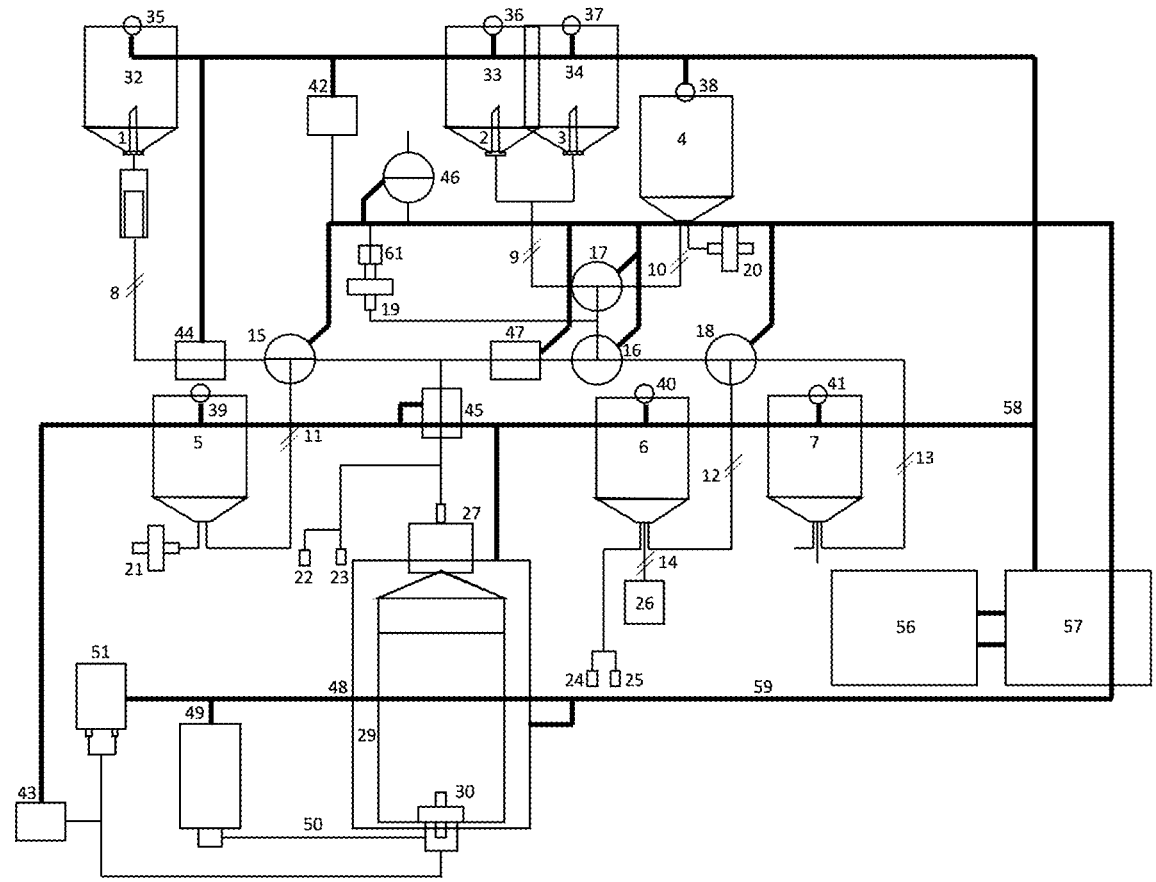
FIG. 3 is a schematic diagram of system input and output design and control principle of the disclosure.
Figure 4:
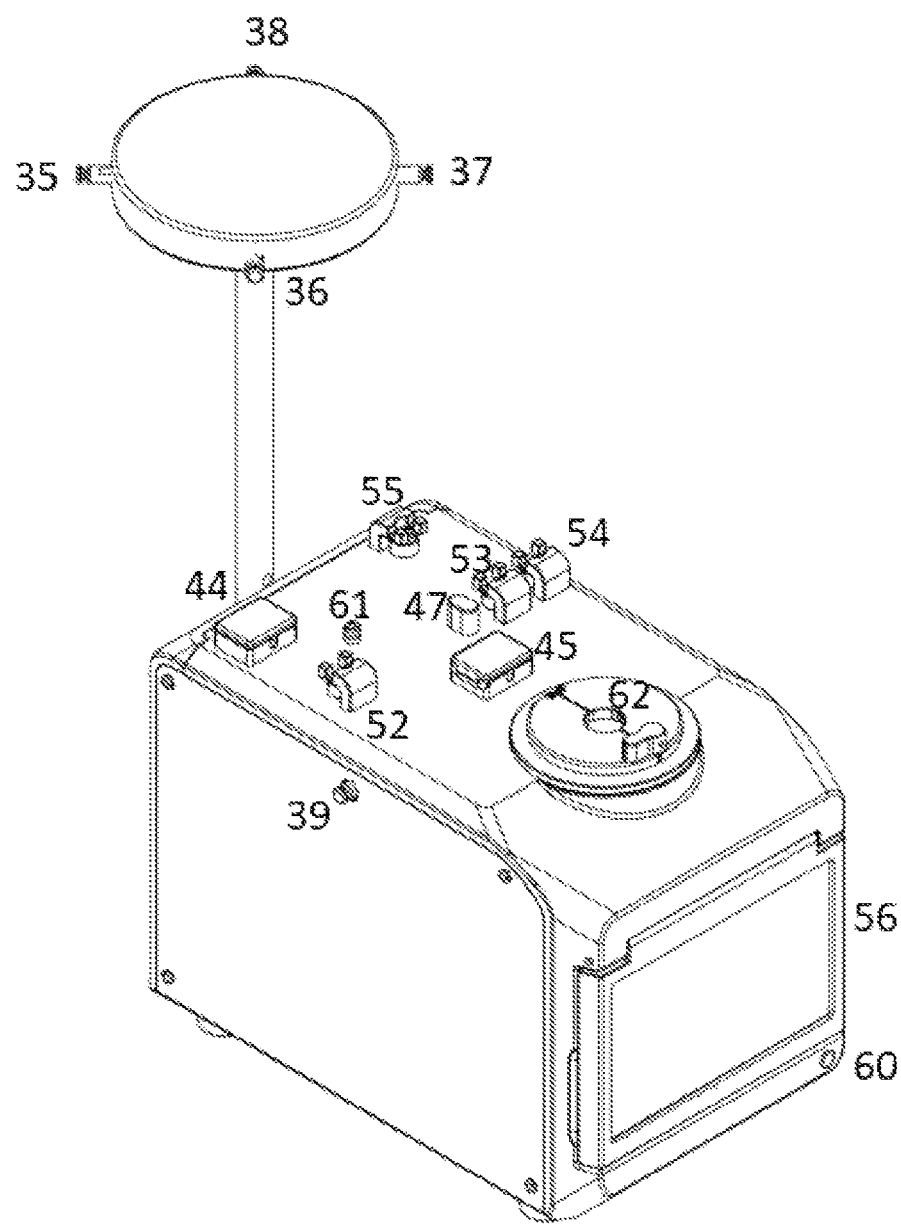
FIG. 4 is a left side view of the shell structure of the disclosure.
Figure 5:
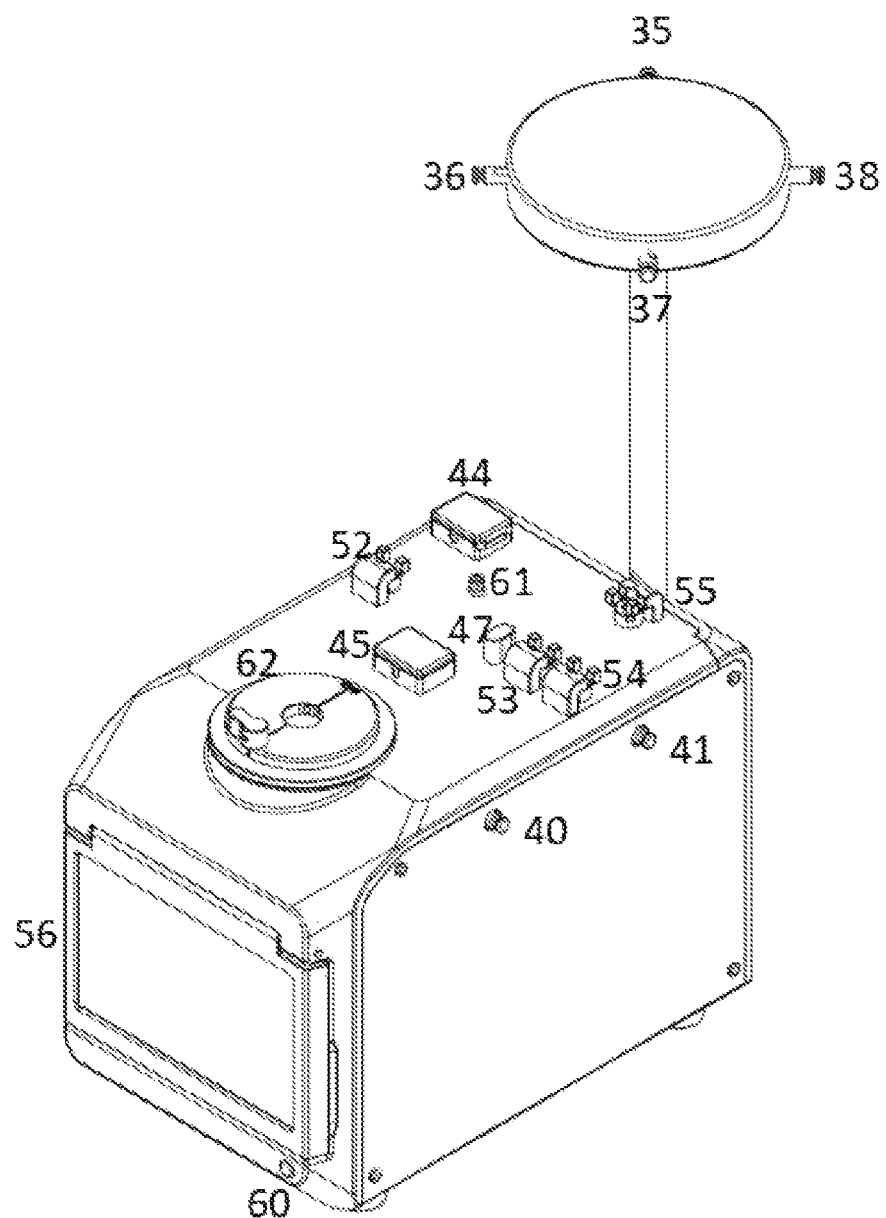
FIG. 5 is a right-side view of the shell structure of the disclosure.
Figure 6:
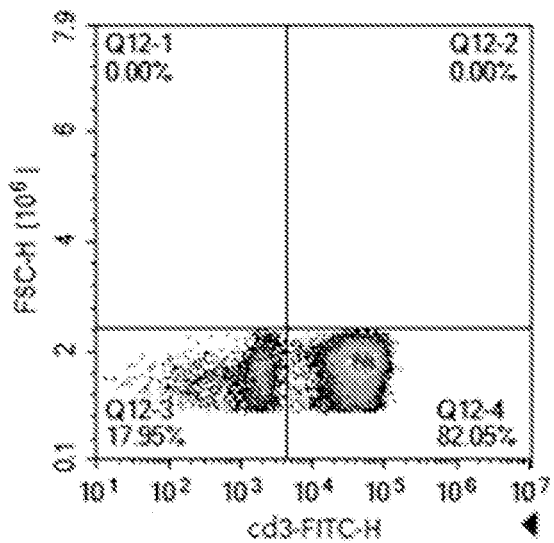
FIG. 6 (A) shows the result of CD3 positive ratio before sorting and FIG. 6 (B) shows the result of CD3 positive ratio after sorting.
Figure 6:
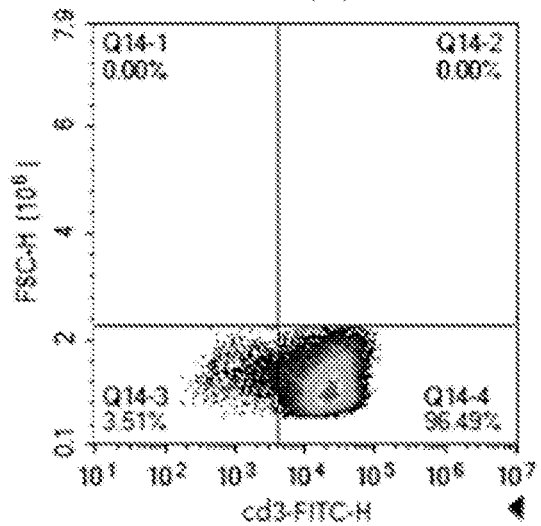

The positive ratio of CD3 before and after sorting is detected by flow cytometry. The results are shown in FIG. 6 (A)-FIG. 6 (B). According to FIG. 6 (A)-(B), the positive ratio after sorting is 96.49%.

c. Cell viability is greater than 90%.

d. CD3+ positive cells are more than 2E7 cells per 100 mL.

In summary, the disclosure provides a device for cells preparation, which has an automatic blood component separator for cell cultivation and preparation, uses a weight sensor to have the weight, and adds a gas intake device and a liquid sensor. By optimizing the connection relationship of each device in the whole equipment, simplifying the operation process of the equipment, coordinating each step of the device, reducing the production cost, integrating the whole technological process, the method makes the cell preparation process more intelligently automated, the operation simpler, the cell pollution reduced and the success rate of cell preparation improved. It has broad application prospects and huge market value.

The disclosure has the following features:

using a self-rotating centrifugal barrel to realize liquid centrifugal separation;

that the centrifugal barrel controls the piston by pneumatic control to achieve the function of pumping liquid and discharging liquid;

accurately controlling the weight of the liquid in the barrel (or converted into volume) by weight sensor, length compensation of liquid pipeline and other parameters;

controlling the liquid flow by rotating the three-way valve to complete the sample separation and collection work;

achieving the adsorption and discharge function of the magnetic beads by the movement of the permanent magnet or the switch of the electromagnet;

achieving cell incubation and other functions by controlling the temperature of the barrel cavity; and that cells can be incubated in a centrifuge for a long time by introducing culture gas.

An important aspect of the present disclosure is to control the amount of liquid in each connected bag or to control the amount of liquid in the centrifugal barrel.

The present disclosure has effective measurement and precise control of inputs (blood sample bags, saline bags, culture medium bags, etc. and outputs including sample collection bags, waste bags, etc.

Further, in the present disclosure, by using the weight sensor to measure the weight change of each bag, the weight and volume of the liquid in the centrifugal barrel can be calculated, and then the length of the liquid path can be further accurately compensated, so that the weight and volume of each part are measured more accurately to achieve better system control effect.

For example 1:

assuming the liquid density of the sample bag is p, the weight change is reduced by M1, the first pipe that is connected to the sample bag can still be measured by the weight sensor, and the length of the pipe is C. The second pipe that is laid on the machine has a length L, the pipe diameter d is 2r, and the weight change in the centrifugal barrel is increased.

If the liquid sensor 2 is used to judge whether there is liquid remaining in the pipeline, if there is no liquid remaining, it can be considered that all the liquid in the pipeline has been sucked into the centrifugal barrel, and the weight of the sample bag is reduced by M1, and it can be inferred that the liquid in the barrel will increase by M1.

The weight sensor and liquid circuit can make the compensation of the weight. Measuring the weight of the sample and solution in each bag directly by the weight sensor is also an important means of precise control of the system. The present disclosure can pre-measure the weight of the consumable bags and the corresponding connecting pipes, and then subtract the actual measured value to get the correct weight of the sample or solution.

For example 2:

Assuming that the mass of the empty solution bags and the corresponding connecting pipes are m, the actual mass measured by the weight sensor is M, and the actual mass of solution in the solution bag is: M−m.

Magnet has played an important role in the present disclosure. Antibody magnetic beads (Notes: immunomagnetic beads or antibody-coupled magnetic nanoparticles) have been used as a means of cell sorting for a long time. The principle is to cross-link antibodies on tiny particles. The principle is to cross-link antibodies on tiny particles, where the antibodies can bind to the antigens on the cell surface, so that the tiny particles can bind to the cells. When passing through the magnetic field, the tiny particles are adsorbed by the magnetic field, while the cells without the particles will pass through the magnetic field, so as to achieve the sorting effect.

The implementation and elimination of the magnetic field can be done in two ways: one is by moving the magnet, and the other is by controlling the switch of the magnet by current.

The magnet can be moved around the pipes through which the cell fluid flows, or the switch of the current-controlled magnet can be controlled to be on or off. The nearer the magnet is, the stronger the magnetic field will be, which will make the adsorption of tiny particles stronger, so that cell sorting can be achieved by designing the corresponding pipeline system, and the cell fluid can flow through the effective magnetic field as long as possible, so that the magnetic separation effect is better.

Cavity temperature control has been implemented in the present disclosure. In the process of cell processing, temperature plays an important role in some cases, and the difference in temperature may even directly affect the quality of the cells after treatment.

The metabolism of the cells can be lowered by cooling, thereby prolonging the tolerance time of the cells in physiological saline. For example, at 37° C., T cells are in physiological saline for 30 minutes, and about 20%-30% of T cells die. If at 4° C., it can be maintained for 3-4 hours, while the cell survival rate is maintained above 95%.

In the process of cell culture, if the temperature is lower than 37° C., the cell doubling time becomes longer and the cell survival rate decreases.

Therefore, temperature control of the centrifugal cavity is an important function of the equipment. The cooling module is used when the temperature is 4° C. to room temperature, while the heating module is used when the temperature is room temperature to 37° C. Equipment can choose not to install temperature control module, or only install one of the temperature control modules, or install two temperature control modules.

Culture gas may be also controlled in the present disclosure. In the process of cell culture, in addition to controlling the temperature of the culture medium, it may be also necessary to control the pH value of the culture medium. The pH value of the culture medium can be controlled by the gas environment outside the culture medium, and commonly used culture gas is 2%-8% carbon dioxide mixed with air.

By opening the pinch valve and the movement of the piston, the culture gas can be taken into the centrifugal barrel, and the culture gas is more fully exchanged with the culture medium in the centrifuge barrel by intermittently rotating left and right of the centrifugal barrel.

The function of the liquid sensors 1 and 2 includes:

determining whether the pipeline is clean, judging whether the consumables are new consumables, and avoiding reuse of disposable consumables; and judging the color of the liquid passing through the sensor.

Especially, the function of the liquid sensor 1 is described in details below: in the process of PBMC separation, slowly laying the blood on the Ficoll is an important technique to achieve high recovery rate and low erythrocyte pollution of PBMC. The system usually fills the centrifuge barrel with Ficol solution and slowly sucks the blood sample into the centrifuge barrel. Since there is some air in the consumable pipe, when air is mixed in the centrifugal barrel filled with Ficol solution, adding a blood sample is equivalent to dropping the blood sample from a high place into the surface of the Ficol solution, which will lead to the impact of Ficol solution on the liquid surface, and change the density of Ficol solution. During the centrifugation process, some PBMC cells penetrate the Ficol solution, which affects the recovery rate of the PBMC;

Therefore, it is a very important process to control the residual air in the centrifuge barrel before adding blood to the Ficol solution.

Figure 7:
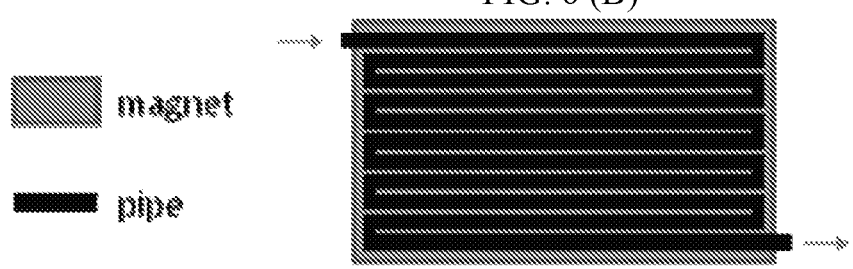
FIG. 7 (A)-FIG. 7 (C) shows different kinds of layout of magnetic device and pipeline, wherein the inner diameter of the pipe is 0.5 mm-4 mm, and magnetic device areas are: 20 mm×20 mm-200 mm×200 mm (the bigger the better, but not too small).
Figure 7:
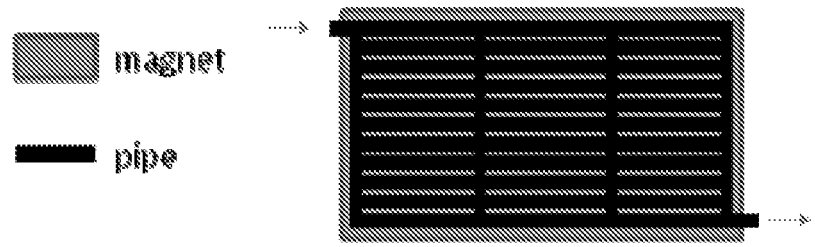
Figure 7:
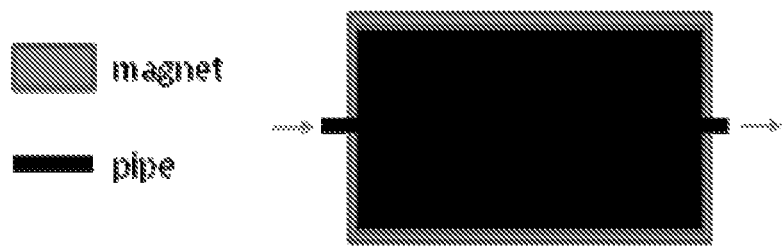

FIG. 7 (A)-FIG. 7 (C) shows different kinds of layout of magnetic device and pipeline, wherein the inner diameter of the pipe is 0.5 mm-4 mm, and magnetic device areas are: 20 mm×20 mm-200 mm×200 mm (the bigger the better, but not too small). In FIG. 7 (A), magnet is in gray color and the pipe is in black color. The magnet is alternatively disposed with the pipe horizontally. Specifically, the magnet and the pipe form an interdigital structure. One pipe is disposed on the left and upper side and another pipe is disposed on the right and bottom side. In FIG. 7(B), the magnet forms three different columns and are disposed inside the pipe. In FIG. 7(C), the pipe is surrounded by the magnet.

Figure 8:
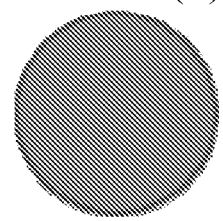
FIG. 8 (A)-FIG. 8(E) show different shapes of the magnetic device, wherein the magnetic device can be square or circular, or a large piece of small magnets, or magnetic array with different magnetic elements.
Figure 8:
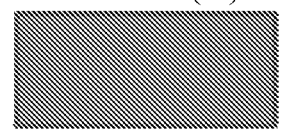
Figure 8:
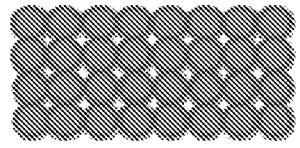
Figure 8:
Figure 8:
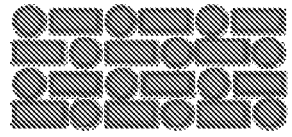

FIG. 8 (A)-FIG. 8(E) show different shapes of the magnetic device, wherein the magnetic device can be square or circular, or a large piece of small magnets, or magnetic array with different magnetic elements, as shown in FIG. 8 (A) to FIG. 8 (E).

The principle of liquid sensor can be referred to FIG. 9 and Table 1.

By emitting light of different wavelengths, it can detect the signal strength of the sensors at the receiving end, and four sets, three sets, and two sets of sensors can be used to judge the liquid in the pipeline.

Table 1 below describes the test results when three sets of sensors are utilized.

TABLE 1 testing results with three sets of sensors

| Detection item | RED | GREEN | BLUE |
|---|---|---|---|
| blank pipe | 310 ± 30 | 230 ± 30 | 500 ± 30 |
| red blood cell | 60 ± 30 | 30 ± 30 | 60 ± 30 |
| buffy coat | 150 ± 30 | 180 ± 30 | 150 ± 30 |
| serum | 300 ± 30 | 500 ± 30 | 600 ± 30 |

For example, for the blank pipe, the strength of the RED is 310±30.

About the function of the liquid sensor 1 is illustrated with the following processes.

(1) initially connect all consumables of the disclosure, connect the centrifuge barrel to the blood sample bag, the blood flow slowly into the blood clot filter, and then slowly enter the subsequent pipe, when liquid sensor 1 is triggered, the injection is stopped;

(2) suck Ficol solution into the centrifugal barrel, and the extra air in the centrifugal bucket is pushed out; and (3) slowly suck the blood sample into the centrifuge barrel and lay it above the Ficol solution.

Rotary valve is utilized to control liquid flow rate. Rotary valves are generally used to control the connection sequence of the liquid pipeline. For example, the two-way valves can control whether the two pipelines are connected. Three-way valves can control whether any two of the three pipelines are connected, or whether all three pipelines are connected or not. The flow rate of the liquid between the connecting pipelines is generally only related to the pipe diameter and the height difference of the liquid surface. To control (reduce) the liquid flow rate, the connecting part of the valve can be dislocated by rotating the angle of the valve, thus reducing the cross-sectional area of liquid flow. However, this method usually does not have a good effect in practical applications. One is that the angle of rotation is not enough to reduce the liquid flow rate; the other is that the rotation is excessive, which directly causes the liquid not to flow.

A structure holding the valve is connected with the valve, and the rotation of a motor drives the valve to rotate. The valve is switched between opening and closing by the clockwise and counterclockwise movement of the motor. By controlling the motor, the opening time of the valve is controlled, so as to control the flow rate of the liquid.

Referring to FIG. 10, FIG. 10 describes the specific control of the flow rate of the liquid by the rotary valve. For example, when the rotary valve is off, the flow rate is zero.

The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments are chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. An apparatus for processing a blood sample, comprising:
   a sample introduction device;
   a centrifugal device;
   a first collection device having a sample acquisition device; and
   a magnetic device having a permanent magnet or an electromagnet, wherein
   the sample introduction device is configured to provide the blood sample to be separated;
   the centrifugation device is used for extracting the blood sample from the sample introduction device and separating at least one component from the blood sample under centrifugal force, and further for pushing the at least one separated component to the first collection device;
   the pipeline between the sample introduction device and the centrifugal device is provided with a first liquid sensor, and the pipeline between the centrifugal device and the first collection device is provided with a second liquid sensor;
   the first liquid sensor is configured to detect a color of a sample flowing through the pipeline when the centrifugal device extracts the blood sample from the sample introduction device;
   the second liquid sensor is configured to detect a color of the at least one separated component flowing through the pipeline when the centrifugal device pushes the at least one separated component to the first collection device;
   the magnetic device is used for applying a fixed or variable magnetic force to a magnetic substance flowing through the pipeline; and
   the linear distance between the magnetic device and the pipeline is variable when a variable magnetic force is applied.

2. The apparatus according to claim 1, further comprising:
   an air extracting/compressor device coupled to the centrifugal device, and
   a gas device coupled to the centrifugal device; wherein
   the centrifugal device extracts the blood sample or pushes the at least one separated component under an action of the air extracting/compressor device;
   the centrifugal device comprises a piston that is for extracting the blood sample or pushing the at least one separated component;
   the centrifugal device comprises a temperature control module to control the temperature inside thereof; and
   the gas device provides a gas environment for cell culture to the centrifugal device.

3. The apparatus according to claim 1, wherein
   the sample introduction device is connected with a first weight sensor; and
   the apparatus calculates the weight of the blood sample drawn by the centrifugal device by a signal of the first weight sensor and parameters of the pipeline through which the blood sample flows into the centrifugal device; and the parameters of the pipeline include one or more of the following: length, diameter, and volume of the pipeline.

4. The apparatus according to claim 3, wherein the first collection device is connected with a second weight sensor; and the apparatus calculates the weight of the at least one separated component pushed by the centrifugal device by a signal of the second weight sensor and parameters of the pipeline through which the at least one separated component flows into the first collection device; and the parameters of the pipeline include one or more of the following: length, diameter, and volume of the pipeline.

5. The apparatus according to claim 4, further comprising:
a second collection device, wherein
along the pipeline, it is sequentially provided with the second liquid sensor, the first collection device and the second collection device;
a first three-way valve is disposed between the first collection device and the second collection device;
the first collection device or the second collection device is a collection bag; and
the first collection device is capable of adding immunomagnetic beads and the immunomagnetic beads can be drawn by the centrifugal device.

6. The apparatus according to claim 5, further comprising:
a third collection device connected with a third weight sensor and
a second three-way valve, wherein
the second three-way valve is disposed between the first liquid sensor and the second liquid sensor along the pipeline, and the second three-way valve is connected to the third collection device; and
the third collection device is a device for accommodating the lymphatic separation medium or waste liquid, and is capable of recovering magnetic beads pushed by the centrifugal device.

7. The apparatus according to claim 6, wherein
along the pipeline, a third three-way valve is disposed between the second liquid sensor and the first collection device;
the third three-way valve is connected with a device for supplying normal saline; and
the device for supplying normal saline is connected with a fourth weight sensor.

8. The apparatus according to claim 7, wherein
along the pipeline, a fourth three-way valve is disposed between the second liquid sensor and the first collection device;
the fourth three-way valve is connected with a device for supplying culture medium; and
the device for supplying culture medium is connected with a fifth weight sensor.

9. The apparatus according to claim 1, wherein
the first liquid sensor or the second liquid sensor includes a light emitting end and a light receiving end, and operates by emitting and receiving light of different wavelengths;
the first liquid sensor or the second liquid sensor is further configured to determine whether the pipeline reaches a predetermined degree of cleanliness; and
a filter for filtering blood clots is provided between the sample introduction device and the first liquid sensor.

10. The apparatus according to claim 1, further comprising
a human interface device, wherein
by the use of the human-machine interface device, or by the use of program module in the human-machine interface device, the apparatus interactively or automatically controls any of the following: the extraction or pushing action of the centrifugal device, and the action of a plurality of valves disposed along the pipeline;
any of the plurality of valves is a rotatable three-way valve; and
for each rotatable three-way valve, a clamping structure is provided to clamp the rotatable three-way valve and the clamping structure is rotated by the motor to drive the rotatable three-way valve to rotate, so as to: control the switching of the rotatable three-way valve between opening and closing by the clockwise and counterclockwise motion of the motor, and control the flow rate of liquid by the duration when the motor opens the rotatable three-way valve.

11. A device for preparing cells, comprising
a sample injection device;
a collecting device;
a fluid supplementation device;
a centrifugal cultivation device;
a liquid sensor device;
a gas exchange device;
a weighing subassembly device; and
a magnetic control device, wherein
the liquid sensor device comprises a first liquid sensor and a second liquid sensor;
the first liquid sensor is connected with the sample injection device;
the second liquid sensor is connected with the centrifugal cultivation device;
the weighing subassembly device comprises a weight sensor that is respectively installed on the sample injection device, the collecting device, the centrifugal cultivation device and the fluid supplementation device; and
the sample injection device, the centrifugal cultivation device, the magnetic control device, the gas exchange device, the fluid supplementation device and the collection device are connected in sequence.

12. The device according to the claim 11, wherein
the sample injection device comprises a blood bag connector, a blood clot filter and a first pipe clamp;
the blood bag connector, the blood clot filter and the first pipe clamp are sequentially connected;
the sample injection device is connected with a first valve through the first liquid sensor;
the centrifugal cultivation device comprises a lymph separation liquid/waste liquid bag and a first liquid filter, a second pipe clamp, the first valve, a first injection port, a second injection port, a temperature control module, a dynamic sealing module, a centrifugal barrel, a piston and the first gas filter;
the first liquid filter, the lymphatic separation liquid/waste liquid bag, the second pipe clamp, the first valve, the second liquid sensor, the first injection port, the second injection port, the dynamic sealing module, the centrifugal barrel and the first gas filter are connected in turn;
the centrifugal barrel comprises a piston inside;
the centrifugal barrel externally comprises a temperature control module;
the device further comprises a centrifugal driving device and a pneumatic device;
the centrifugal driving device comprises an electric rotating motor and a transmission device;
the pneumatic device comprises a first gas pressure detector and a pneumatic control device;
the centrifugal driving device is connected with a centrifugal cultivation device;
the pneumatic device is connected with a centrifugal cultivation device;

the gas exchange device comprises a second gas pressure detector, a fifth valve and a gas route joint;

the fifth valve, the second gas pressure detector and the gas route joint are connected in turn;

the fluid supplementation device comprises a normal saline connector, a cultivation medium bag, a third pipe clamp, a third valve, a fourth valve, a fourth pipe clamp and a second liquid filter;

the normal saline connector is connected sequentially with the fourth valve through the third pipe clamp;

the second liquid filter, the medium bag, the fourth pipe clamp and the fourth valve are connected in turn, and the third valve and the fourth valve are connected in turn;

the collection device comprises a sixth valve, a fifth pipe clamp, a sixth pipe clamp, a seventh pipe clamp, a first collection bag, a second collection bag, a third injection port, a fourth injection port and a sampling bag;

the sampling bag, the fifth pipe clamp, the first collecting bag, and the sixth pipe clamp and the sixth valve are connected in sequence;

the second collection bag is connected with the sixth valve through the seventh pipe clamp; and the first collection bag is also connected with a third injection port and a fourth injection port.

13. The device according to claim 11, wherein the magnetic control device comprises a controllable magnet; and the controllable magnet includes permanent magnets or non-permanent magnets; and valves disposed along a pipeline of the device include one or more of solenoid valves, pinch valves or rotary valves.

14. The device according to claim 11, further comprising;

a shell structure, wherein the shell structure is embedded with a valve rotating mechanism, a centrifugal barrel clamp, a first liquid sensor, a second liquid sensor, a gas path joint and a controllable magnet;

the shell structure is distributed with 2-10 weight sensors; and the shell structure includes a human-machine interface.

15. A method for preparing cells using the device according to claim 11, comprising the following steps:

step (1) gradient centrifugation is used to centrifuge in the centrifugal cultivation device; the liquid flow is regulated by liquid sensor device, centrifugal cultivation device and weighing subassembly device, and the cells in the sample are separated into collection device; and step (2) the antibody magnetic beads are added to the cells collected in step (1) and transferred to the centrifugal cultivation device, The target cells are separated by the magnetic control device, and then the cells are collected by the collection device.

16. The method according to claim 15, wherein the method includes an initialization step before the step (1);

the initialization steps include preparing samples, connecting consumables, and self-checking.

17. The method according to claim 16, wherein the consumables include a blood sample bag, a lymphatic separation liquid/waste liquid bag, a first collection bag, a second collection bag, a normal saline bag, a medium bag and a centrifugal barrel.

18. The method according to claim 15, wherein the method includes a step of flushing the pipeline after the step (1) and before the step (2);

the steps of the flushing the pipeline are as follows: the normal saline in the fluid supplementation device is pumped into the centrifugal barrel and discharged into the lymphatic separation liquid bag; and the number of the flushing the pipeline is 1-6 times.

19. The method according to claim 11, wherein the method further includes the following steps:

(1) samples are prepared, consumables are connected and self-checked;

the consumables include a blood sample bag, a lymphatic separation liquid/waste liquid bag, a first collection bag, a second collection bag, a normal saline bag, a cultivation medium bag and a centrifugal barrel;

the gradient centrifugation method is used to centrifuge in the centrifugal cultivation device;

the liquid flow is regulated by the liquid sensor device, the centrifugal cultivation device and the weighting subassembly device, and the cells in the sample are separated into the collection device; the normal saline in the fluid supplementation device is pumped into the centrifugal barrel and then discharged to the lymph separation liquid/waste liquid bag that repeated many times;

(2) the antibody magnetic beads are added to the cells collected in step (1) and transferred to the centrifugal cultivation device; the target cells are separated by a magnetic control device;

(3) adding magnetic beads to the target cells separated in step (2) to remove enzymes;

after mixed incubation in a centrifugal cultivation device, removing magnetic beads through a magnetic control device, and then collecting cells by a collection device.

20. An apparatus for processing a blood sample, comprising:

a sample introduction device;

a centrifugal device;

a first collection device having a sample acquisition device;

an air extracting/compressor device coupled to the centrifugal device, and a gas device coupled to the centrifugal device; wherein the sample introduction device is configured to provide the blood sample to be separated;

the centrifugation device is used for extracting the blood sample from the sample introduction device and separating at least one component from the blood sample under centrifugal force, and further for pushing the at least one separated component to the first collection device;

the pipeline between the sample introduction device and the centrifugal device is provided with a first liquid sensor, and the pipeline between the centrifugal device and the first collection device is provided with a second liquid sensor;

the first liquid sensor is configured to detect a color of a sample flowing through the pipeline when the centrifugal device extracts the blood sample from the sample introduction device;

the second liquid sensor is configured to detect a color of the at least one separated component flowing through the pipeline when the centrifugal device pushes the at least one separated component to the first collection device;

the centrifugal device extracts the blood sample or pushes the at least one separated component under an action of the air extracting/compressor device;

the centrifugal device comprises a piston that is for extracting the blood sample or pushing the at least one separated component;

the centrifugal device comprises a temperature control module to control the temperature inside thereof; and the gas device provides a gas environment for cell culture to the centrifugal device.

21. The apparatus according to claim 20, wherein the sample introduction device is connected with a first weight sensor; and the apparatus calculates the weight of the blood sample drawn by the centrifugal device by a signal of the first weight sensor and parameters of the pipeline through which the blood sample flows into the centrifugal device; and the parameters of the pipeline include one or more of the following: length, diameter, and volume of the pipeline.

22. The apparatus according to claim 21, wherein the first collection device is connected with a second weight sensor; and the apparatus calculates the weight of the at least one separated component pushed by the centrifugal device by a signal of the second weight sensor and parameters of the pipeline through which the at least one separated component flows into the first collection device; and the parameters of the pipeline include one or more of the following: length, diameter, and volume of the pipeline.

23. The apparatus according to claim 22, further comprising:

a second collection device, wherein along the pipeline, it is sequentially provided with the second liquid sensor, the first collection device and the second collection device;

a first three-way valve is disposed between the first collection device and the second collection device;

the first collection device or the second collection device is a collection bag; and the first collection device is capable of adding immunomagnetic beads and the immunomagnetic beads can be drawn by the centrifugal device.

24. The apparatus according to claim 23, further comprising:

a third collection device connected with a third weight sensor and a second three-way valve, wherein the second three-way valve is disposed between the first liquid sensor and the second liquid sensor along the pipeline, and the second three-way valve is connected to the third collection device; and the third collection device is a device for accommodating the lymphatic separation medium or waste liquid, and is capable of recovering magnetic beads pushed by the centrifugal device.

25. The apparatus according to claim 24, wherein along the pipeline, a third three-way valve is disposed between the second liquid sensor and the first collection device;

the third three-way valve is connected with a device for supplying normal saline; and the device for supplying normal saline is connected with a fourth weight sensor.

26. The apparatus according to claim 25, wherein along the pipeline, a fourth three-way valve is disposed between the second liquid sensor and the first collection device;

the fourth three-way valve is connected with a device for supplying culture medium; and the device for supplying culture medium is connected with a fifth weight sensor.

27. The apparatus according to claim 20, wherein the first liquid sensor or the second liquid sensor includes a light emitting end and a light receiving end, and operates by emitting and receiving light of different wavelengths;

the first liquid sensor or the second liquid sensor is further configured to determine whether the pipeline reaches a predetermined degree of cleanliness; and a filter for filtering blood clots is provided between the sample introduction device and the first liquid sensor.

28. The apparatus according to claim 20, further comprising a human interface device, wherein by the use of the human-machine interface device, or by the use of program module in the human-machine interface device, the apparatus interactively or automatically controls any of the following: the extraction or pushing action of the centrifugal device, and the action of a plurality of valves disposed along the pipeline;

any of the plurality of valves is a rotatable three-way valve; and for each rotatable three-way valve, a clamping structure is provided to clamp the rotatable three-way valve and the clamping structure is rotated by the motor to drive the rotatable three-way valve to rotate, so as to: control the switching of the rotatable three-way valve between opening and closing by the clockwise and counter-clockwise motion of the motor, and control the flow rate of liquid by the duration when the motor opens the rotatable three-way valve.

* * * * *